(12) United States Patent
Bhattacharya

(10) Patent No.: US 12,324,662 B2
(45) Date of Patent: Jun. 10, 2025

(54) SYSTEMS, DEVICES, AND METHODS FOR SENSOR FAULT DETECTION

(71) Applicant: ABBOTT DIABETES CARE INC., Alameda, CA (US)

(72) Inventor: Aparajita Bhattacharya, Dublin, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 962 days.

(21) Appl. No.: 17/224,561

(22) Filed: Apr. 7, 2021

(65) Prior Publication Data

US 2021/0219879 A1    Jul. 22, 2021

Related U.S. Application Data

(63) Continuation of application No. PCT/US2019/055338, filed on Oct. 9, 2019.

(60) Provisional application No. 62/744,646, filed on Oct. 12, 2018.

(51) Int. Cl.
*A61B 5/145* (2006.01)
*A61B 5/00* (2006.01)

(52) U.S. Cl.
CPC ........ *A61B 5/14532* (2013.01); *A61B 5/0004* (2013.01); *A61B 5/14503* (2013.01); *A61B 5/7405* (2013.01); *A61B 5/742* (2013.01)

(58) Field of Classification Search
CPC .. A61B 5/14503–14546; A61B 5/0004; A61B 5/74–746; A61B 2560/0276; A61B 5/7271–7275; A61B 5/0022; A61B 5/7405; A61B 5/1495; G16H 40/40
See application file for complete search history.

(56) References Cited

U.S. PATENT DOCUMENTS

| | | |
|---|---|---|
| 5,913,828 A | 6/1999 | Russell |
| 2008/0009692 A1 | 1/2008 | Stafford |
| 2010/0057041 A1 | 3/2010 | Hayter |
| 2011/0193704 A1 | 8/2011 | Harper et al. |
| 2011/0213225 A1 | 9/2011 | Bernstein et al. |
| 2011/0319729 A1 | 12/2011 | Donnay et al. |
| 2015/0018639 A1 | 1/2015 | Stafford |
| 2015/0025345 A1 | 1/2015 | Funderburk et al. |
| 2015/0173661 A1 | 6/2015 | Myles |
| 2016/0022221 A1* | 1/2016 | Ou ..................... A61B 5/14532 600/365 |
| 2016/0296148 A1* | 10/2016 | Hayter ................. A61B 5/0022 |

FOREIGN PATENT DOCUMENTS

| | | | |
|---|---|---|---|
| CN | 108544925 A | * | 9/2018 |
| JP | 2011-125633 | | 6/2011 |
| WO | WO-02058537 A2 | * | 8/2002 ........... A61B 5/0002 |

OTHER PUBLICATIONS

Englsih Translation of CN 108544925 A, Beijing Institute of Technology BIT, 9 pages, printed on Jul. 30, 2024, (Year: 2018).*

(Continued)

*Primary Examiner* — Devin B Henson
*Assistant Examiner* — Jennifer Grace Baires-Tweed
(74) *Attorney, Agent, or Firm* — ONE LLP

(57) ABSTRACT

Various embodiments of systems, devices and methods for detecting a sensor fault in an analyte sensor are disclosed. These embodiments utilize analyte metrics and thresholds.

18 Claims, 5 Drawing Sheets

(56) References Cited

OTHER PUBLICATIONS

JP, 2021-516747 Office Action, Jun. 21, 2023.
EP, 19872209.2 Examination Report, Nov. 6, 2023.
CA, 3,116,033 Examiner's Report, Mar. 15, 2023.
EP, 19872209.2 Extended Search Report, Jun. 21, 2022.
WO, PCT/US2019/055338 ISR and Written Opinion, Jan. 2, 2020.
CN, 201980066992.9 First Office Action, Feb. 26, 2024.
JP, 2021-516747 Second Office Action, Dec. 13, 2023.
MX, MX/a/2021/004217 Office Action, Apr. 12, 2024.
AU, 2019356913 First Examination Report, Sep. 27, 2024.
CN, 201980066992.9 Second Office Action, Aug. 19, 2024.
MY, PI2021001901 Office Action, Oct. 25, 2024.

* cited by examiner

SYSTEMS, DEVICES, AND METHODS FOR SENSOR FAULT DETECTION

CROSS-REFERENCE TO RELATED APPLICATIONS

The present application is a continuation of International Patent Application No. PCT/US2019/055338, filed Oct. 9, 2019, which claims priority to and the benefit of U.S. Provisional Patent Application No. 62/744,646, filed Oct. 12, 2018, both of which are incorporated by reference herein in their entirety for all purposes.

FIELD

The subject matter described herein relates generally to systems, devices, and methods for sensor fault detection.

BACKGROUND

A vast and growing market exists for monitoring the health and condition of humans and other living animals. Information that describes the physical or physiological condition of humans can be used in countless ways to assist and improve quality of life, and diagnose and treat undesirable human conditions.

A common device used to collect such information is a physiological sensor such as a biochemical analyte sensor, or a device capable of sensing a chemical analyte of a biological entity. Biochemical sensors come in many forms and can be used to sense analytes in fluids, tissues, or gases forming part of, or produced by, a biological entity, such as a human being. These analyte sensors can be used on or within the body itself, or they can be used on biological substances that have already been removed from the body.

Although analyte sensors often have a complex and well-studied design, they can still be subject to an unexpected loss of function prior to the end of their expected life. For example, in some instances, moisture entering a sealed portion of an on-body sensor unit of an analyte monitoring system can cause a disruption to an electrical signal path of the sensor. This can result in one or more of the following: intermittent spikes, data being disqualified by existing data quality checks, observed high instantaneous rates of analyte change, or very high analyte level readings.

Certain known methods can detect and remove some of these aforementioned artifacts and prevent them from affecting the final analyte level readings presented by an analyte monitoring system. These existing methods, however, may not prevent all cases. If these known methods fail to detect such artifacts, the consequences can be harmful to the patient. For example, artifacts that inaccurately reflect high analyte level readings can potentially mislead a patient to incorrectly administer or increase a medication dosage.

For these and other reasons, needs exist for improvement to the detection of sensor faults in analyte sensors.

SUMMARY

Example embodiments of systems, devices, and methods are described herein for fault detection in an analyte sensor. These embodiments provide for the detection of sensor fault based on one or more calculated metrics, and one or more thresholds based on the calculated metrics. According to some embodiments, for example, an indication of a suspected sensor fault can be generated when a predetermined rate of analyte level change threshold and a predetermined analyte level sum threshold are exceeded. Numerous examples of algorithms and methods for performing combinations and/or variations of one or both of these detection mechanisms are provided, as well as example embodiments of systems and devices for performing the same.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1:
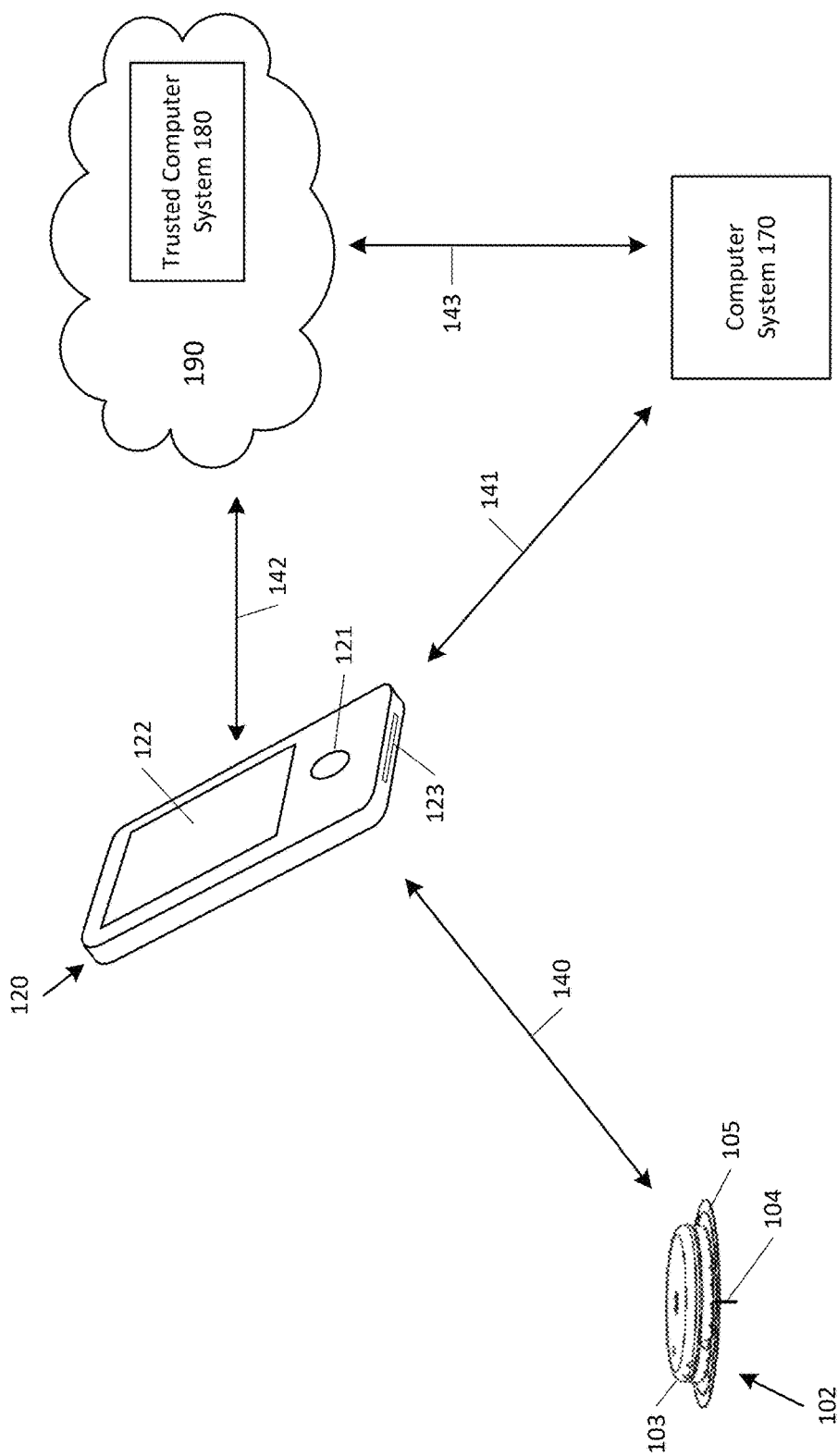
FIG. 1 is an illustrative view depicting an example embodiment of an in vivo analyte monitoring system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The publications discussed herein are provided solely for their disclosure prior to the filing date of the present application. Nothing herein is to be construed as an admission that the present disclosure is not entitled to antedate such publications by virtue of prior disclosure. Furthermore, the dates of publication provided may be different from the actual publication dates which may need to be independently confirmed.

Generally, embodiments of the present disclosure are used with systems, devices, and methods for detecting at least one analyte, such as glucose, in a bodily fluid (e.g., subcutaneously within the interstitial fluid ("ISF") or blood, within the dermal fluid of the dermal layer, or otherwise). Accordingly, many embodiments include in vivo analyte sensors structurally configured so that at least a portion of the sensor is, or can be, positioned in the body of a user to obtain information about at least one analyte of the body. However, the embodiments disclosed herein can be used with in vivo analyte monitoring systems that incorporate in vitro capability, as well as purely in vitro or ex vivo analyte monitoring systems, including those systems that are entirely non-invasive.

Furthermore, for each and every embodiment of a method disclosed herein, systems and devices capable of performing each of those embodiments are covered within the scope of the present disclosure. For example, embodiments of sensor control devices are disclosed, and these devices can have one or more sensors, analyte monitoring circuitry (e.g., an analog circuit), non-transitory memories (e.g., for storing instructions), power sources, communication circuitry, transmitters, receivers, processing circuitry, and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

Likewise, embodiments of reader devices are disclosed having one or more transmitters, receivers, non-transitory memories (e.g., for storing instructions), power sources, processing circuitry, and/or controllers (e.g., for executing instructions) that can perform any and all method steps or facilitate the execution of any and all method steps. These embodiments of the reader devices can be used to implement those steps performed by a reader device from any and all of the methods described herein.

Embodiments of trusted computer systems are also disclosed. These trusted computer systems can include one or more processing circuitry, controllers, transmitters, receivers, non-transitory memories, databases, servers, and/or networks, and can be discretely located or distributed across multiple geographic locales. These embodiments of the trusted computer systems can be used to implement those steps performed by a trusted computer system from any and all of the methods described herein.

A number of embodiments of the present disclosure are designed to improve upon the computer-implemented capabilities of analyte monitoring systems with respect to the detection of a suspected sensor fault. In some embodiments, for example, a sensor control device is worn on the body, where the sensor control device includes an in vivo analyte sensor. According to one aspect of the embodiments, sensor data received from the analyte sensor can be periodically received and analyte metrics calculated by processing circuitry of a sensor control device. The analyte metrics can include, for example, a rate of analyte level change and/or a sum of analyte levels within a predetermined time window. Based on the analyte metrics, the processing circuitry can detect a suspected sensor fault in the analyte sensor.

Accordingly, the embodiments disclosed herein reflect improvements over prior methods for sensor fault detection. For example, the embodiments can provide for a more robust method of sensor fault detection by reducing the number of false positives by utilizing multiple threshold conditions. Consequently, the embodiments described herein are directed to systems, devices, and methods that can improve upon the accuracy of analyte monitoring systems by utilizing analyte sensor data in a specific and non-conventional way, and by informing the user, in a timely manner, when a suspected sensor fault is detected and/or when an analyte sensor should be replaced. Other features and advantages of the disclosed embodiments are further discussed below.

Before describing the embodiments in detail, however, it is first desirable to describe examples of devices that can be present within, for example, an in vivo analyte monitoring system, as well as examples of their operation, all of which can be used with the embodiments described herein.

Example Embodiments of Analyte Monitoring Systems

There are various types of analyte monitoring systems. "Continuous Analyte Monitoring" systems (or "Continuous Glucose Monitoring" systems), for example, are in vivo systems that can transmit data from a sensor control device to a reader device repeatedly or continuously without prompting, e.g., automatically according to a schedule. "Flash Analyte Monitoring" systems (or "Flash Glucose Monitoring" systems or simply "Flash" systems), as another example, are in vivo systems that can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo monitoring systems can include a sensor that, while positioned in vivo, makes contact with the bodily fluid of the user and senses one or more analyte levels contained therein. The sensor can be part of a sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few. As used herein, these terms are not limited to devices with analyte sensors, and encompass devices that have sensors of other types, whether biometric or non-biometric. The term "on body" refers to any device that resides directly on the body or in close proximity to the body, such as a wearable device (e.g., glasses, watch, wristband or bracelet, neckband or necklace, etc.).

In vivo monitoring systems can also include one or more reader devices that receive sensed analyte data from the sensor control device. These reader devices can process and/or display the sensed analyte data, or sensor data, in any number of forms, to the user. These devices, and variations thereof, can be referred to as "handheld reader devices," "reader devices" (or simply, "readers"), "handheld electronics" (or handhelds), "portable data processing" devices or units, "data receivers," "receiver" devices or units (or simply receivers), "relay" devices or units, or "remote" devices or units, to name a few. Other devices such as personal computers have also been utilized with or incorporated into in vivo and in vitro monitoring systems.

In vivo analyte monitoring systems can be differentiated from "in vitro" systems that contact a biological sample outside of the body (or rather "ex vivo") and that typically include a meter device that has a port for receiving an analyte test strip carrying a bodily fluid of the user, which can be analyzed to determine the user's analyte level. As mentioned, the embodiments described herein can be used with in vivo systems, in vitro systems, and combinations thereof.

The embodiments described herein can be used to monitor and/or process information regarding any number of one or more different analytes. Analytes that may be monitored include, but are not limited to, acetyl choline, amylase, bilirubin, cholesterol, chorionic gonadotropin, glycosylated hemoglobin (HbAlc), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

FIG. 1 is an illustrative view depicting an example embodiment of an in vivo analyte monitoring system 100 having a sensor control device 102 and a reader device 120 that communicate with each other over a local communication path (or link) 140, which can be wired or wireless, and uni-directional or bi-directional. In embodiments where path 140 is wireless, a near field communication (NFC) protocol, RFID protocol, Bluetooth or Bluetooth Low Energy protocol, Wi-Fi protocol, proprietary protocol, or the like can be used, including those communication protocols in existence as of the date of this filing or their later developed variants.

Reader device 120 is also capable of wired, wireless, or combined communication with a computer system 170 (e.g., a local or remote computer system) over communication path (or link) 141 and with a network 190, such as the internet or the cloud, over communication path (or link) 142. Communication with network 190 can involve communication with trusted computer system 180 within network 190, or though network 190 to computer system 170 via communication link (or path) 143. Communication paths 141, 142, and 143 can be wireless, wired, or both, can be uni-directional or bi-directional, and can be part of a telecommunications network, such as a Wi-Fi network, a local area network (LAN), a wide area network (WAN), the internet, or other data network. In some cases, communication paths 141 and 142 can be the same path. All communications over paths 140, 141, and 142 can be encrypted and sensor control device 102, reader device 120, computer system 170, and trusted computer system 180 can each be configured to encrypt and decrypt those communications sent and received.

Variants of devices 102 and 120, as well as other components of an in vivo-based analyte monitoring system that are suitable for use with the system, device, and method embodiments set forth herein, are described in U.S. Patent Publication No. 2011/0213225 (the '225 Publication), which is incorporated by reference herein in its entirety for all purposes.

Sensor control device 102 can include a housing 103 containing in vivo analyte monitoring circuitry and a power source. In this embodiment, the in vivo analyte monitoring circuitry is electrically coupled with an analyte sensor 104 that extends through an adhesive patch 105 and projects away from housing 103. Adhesive patch 105 contains an adhesive layer (not shown) for attachment to a skin surface of the body of the user. Other forms of body attachment to the body may be used, in addition to or instead of adhesive.

Sensor 104 is adapted to be at least partially inserted into the body of the user, where it can make fluid contact with that user's bodily fluid (e.g., subcutaneous (subdermal) fluid, dermal fluid, or blood) and be used, along with the in vivo analyte monitoring circuitry, to measure analyte-related data of the user. Sensor 104 and any accompanying sensor control electronics can be applied to the body in any desired manner. For example, an insertion device (not shown) can be used to position all or a portion of analyte sensor 104 through an external surface of the user's skin and into contact with the user's bodily fluid. In doing so, the insertion device can also position sensor control device 102 with adhesive patch 105 onto the skin. In other embodiments, insertion device can position sensor 104 first, and then accompanying sensor control electronics can be coupled with sensor 104 afterwards, either manually or with the aid of a mechanical device. Examples of insertion devices are described in U.S. Patent Publication Nos. 2008/0009692, 2011/0319729, 2015/0018639, 2015/0025345, and 2015/0173661, all which are incorporated by reference herein in their entireties and for all purposes.

After collecting raw data from the user's body, sensor control device 102 can apply analog signal conditioning to the data and convert the data into a digital form of the conditioned raw data. In some embodiments, sensor control device 102 can then algorithmically process the digital raw data into a form that is representative of the user's measured biometric (e.g., analyte level) and/or one or more analyte metrics based thereupon. For example, sensor control device 102 can include processing circuitry to algorithmically perform any of the method steps described herein to calculate analyte metrics utilized to detect a sensor fault by the analyte sensor. Sensor control device 102 can then encode and wirelessly communicate the calculated analyte metrics, indications of sensor fault and/or processed sensor data to reader device 120, which in turn can format or graphically process the received data for digital display to the user. In other embodiments, in addition to, or in lieu of, wirelessly communicating sensor data to another device (e.g., reader device 120), sensor control device 102 can graphically process the final form of the data such that it is ready for display, and display that data on a display of sensor control device 102. In some embodiments, the final form of the biometric data (prior to graphic processing) is used by the system (e.g., incorporated into a diabetes monitoring regime) without processing for display to the user.

In still other embodiments, the conditioned raw digital data can be encoded for transmission to another device, e.g., reader device 120, which then algorithmically processes that digital raw data into a form representative of the user's measured biometric (e.g., a form readily made suitable for display to the user) and/or one or more analyte metrics based thereupon. Reader device 120 can include processing circuitry to algorithmically perform any of the method steps described herein to calculate analyte metrics utilized to detect a fault in the analyte sensor. This algorithmically processed data can then be formatted or graphically processed for digital display to the user.

In other embodiments, sensor control device 102 and reader device 120 transmit the digital raw data to another computer system for algorithmic processing and display.

Reader device 120 can include a display 122 to output information to the user and/or to accept an input from the user, and an optional input component 121 (or more), such as a button, actuator, touch sensitive switch, capacitive switch, pressure sensitive switch, jog wheel or the like, to input data, commands, or otherwise control the operation of reader device 120. In certain embodiments, display 122 and input component 121 may be integrated into a single component, for example, where the display can detect the presence and location of a physical contact touch upon the display, such as a touch screen user interface. In certain embodiments, input component 121 of reader device 120 may include a microphone and reader device 120 may include software configured to analyze audio input received from the microphone, such that functions and operation of the reader device 120 may be controlled by voice commands. In certain embodiments, an output component of reader device 120 includes a speaker (not shown) for outputting information as audible signals. Similar voice responsive components such as a speaker, microphone and software routines to generate, process and store voice driven signals may be included in sensor control device 102.

Reader device 120 can also include one or more data communication ports 123 for wired data communication with external devices such as computer system 170 or sensor control device 102. Example data communication ports include USB ports, mini USB ports, USB Type-C ports, USB micro-A and/or micro-B ports, RS-232 ports, Ethernet ports, Firewire ports, or other similar data communication ports configured to connect to the compatible data cables. Reader device 120 may also include an integrated or attachable in vitro glucose meter, including an in vitro test strip port (not shown) to receive an in vitro glucose test strip for performing in vitro blood glucose measurements.

Reader device 120 can display the measured biometric data wirelessly received from sensor control device 102 and can also be configured to output alarms, alert notifications, glucose values, etc., which may be visual, audible, tactile, or any combination thereof. Further details and other display embodiments can be found in, e.g., U.S. Patent Publication No. 2011/0193704, which is incorporated herein by reference in its entirety for all purposes.

Reader device 120 can function as a data conduit to transfer the measured data and/or analyte metrics from sensor control device 102 to computer system 170 or trusted computer system 180. In certain embodiments, the data received from sensor control device 102 may be stored (permanently or temporarily) in one or more memories of reader device 120 prior to uploading to system 170, 180 or network 190.

Computer system 170 may be a personal computer, a server terminal, a laptop computer, a tablet, or other suitable data processing device. Computer system 170 can be (or include) software for data management and analysis and communication with the components in analyte monitoring system 100. Computer system 170 can be used by the user or a medical professional to display and/or analyze the biometric data measured by sensor control device 102. In some embodiments, sensor control device 102 can communicate the biometric data directly to computer system 170 without an intermediary such as reader device 120, or indirectly using an internet connection (also optionally without first sending to reader device 120). Operation and use of computer system 170 is further described in the '225 Publication incorporated herein. Analyte monitoring system 100 can also be configured to operate with a data processing module (not shown), also as described in the incorporated '225 Publication.

Trusted computer system 180 can be within the possession of the manufacturer or distributor of sensor control device 102, either physically or virtually through a secured connection, and can be used to perform authentication of sensor control device 102, for secure storage of the user's biometric data, and/or as a server that serves a data analytics program (e.g., accessible via a web browser) for performing analysis on the user's measured data.

Example Embodiments of Reader Devices

Reader device 120 can be a mobile communication device such as a dedicated reader device (configured for communication with a sensor control device 102, and optionally a computer system 170, but without mobile telephony communication capability) or a mobile telephone including, but not limited to, a Wi-Fi or internet enabled smart phone, tablet, or personal digital assistant (PDA). Examples of smart phones can include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as Google glasses, which is a mobile communication device). This optical assembly can have a transparent display that displays information about the user's analyte level (as described herein) to the user while at the same time allowing the user to see through the display such that the user's overall vision is minimally obstructed. The optical assembly may be capable of wireless communications similar to a smart phone. Other examples of wearable electronics include devices that are worn around or in the proximity of the user's wrist (e.g., a watch, etc.), neck (e.g., a necklace, etc.), head (e.g., a headband, hat, etc.), chest, or the like.

Figure 2:
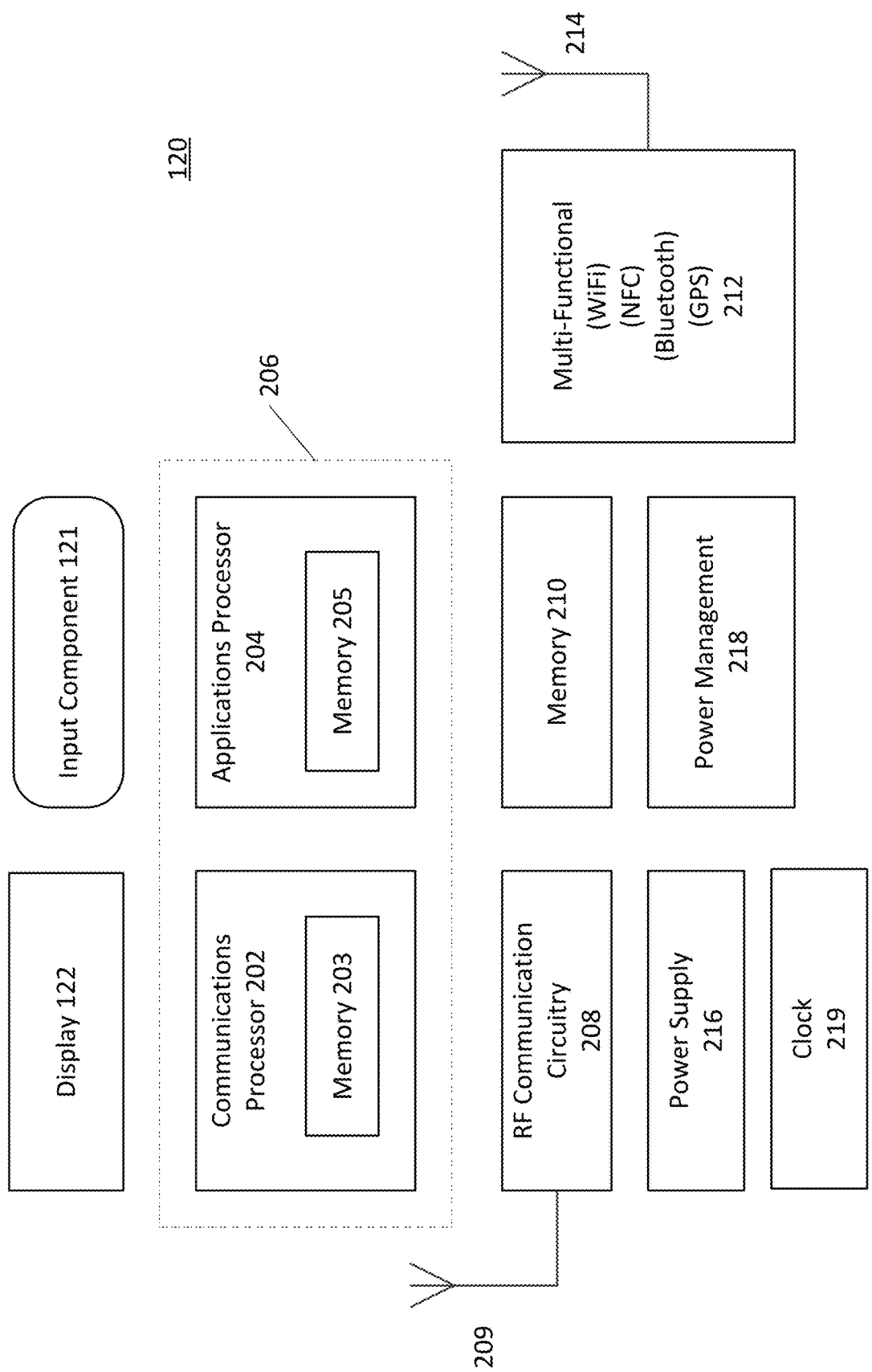
FIG. 2 is a block diagram of an example embodiment of a reader device.

FIG. 2 is a block diagram of an example embodiment of a reader device 120 configured as a smart phone. Here, reader device 120 includes an input component 121, display 122, and processing circuitry 206, which can include one or more processors, microprocessors, controllers, and/or microcontrollers, each of which can be a discrete chip or distributed amongst (and a portion of) a number of different chips. Here, processing circuitry 206 includes a communications processor 202 having on-board memory 203 and an applications processor 204 having on-board memory 205. Reader device 120 further includes RF communication circuitry 208 coupled with an RF antenna 209, a memory 210, multi-functional circuitry 212 with one or more associated antennas 214, a power supply 216, power management circuitry 218, and a clock 219. FIG. 2 is an abbreviated representation of the typical hardware and functionality that resides within a smart phone and those of ordinary skill in the art will readily recognize that other hardware and functionality (e.g., codecs, drivers, glue logic) can also be included.

Communications processor 202 can interface with RF communication circuitry 208 and perform analog-to-digital conversions, encoding and decoding, digital signal processing and other functions that facilitate the conversion of voice, video, and data signals into a format (e.g., in-phase and quadrature) suitable for provision to RF communication circuitry 208, which can then transmit the signals wirelessly. Communications processor 202 can also interface with RF communication circuitry 208 to perform the reverse functions necessary to receive a wireless transmission and convert it into digital data, voice, and video. RF communication circuitry 208 can include a transmitter and a receiver (e.g., integrated as a transceiver) and associated encoder logic.

Applications processor 204 can be adapted to execute the operating system and any software applications that reside on reader device 120, process video and graphics, and perform those other functions not related to the processing of communications transmitted and received over RF antenna 209. The smart phone operating system will operate in conjunction with a number of applications on reader device 120. Any number of applications (also known as "user interface applications") can be running on reader device 120 at any one time, and may include one or more applications that are related to a diabetes monitoring regime, in addition to the other commonly used applications that are unrelated to such a regime, e.g., email, calendar, weather, sports, games, etc. For example, the data indicative of a sensed analyte level and in vitro blood analyte measurements received by the reader device can be securely communicated to user interface applications residing in memory 210 of reader device 120. Such communications can be securely performed, for example, through the use of mobile application containerization or wrapping technologies.

Memory 210 can be shared by one or more of the various functional units present within reader device 120, or can be distributed amongst two or more of them (e.g., as separate memories present within different chips). Memory 210 can also be a separate chip of its own. Memories 203, 205, and 210 are non-transitory, and can be volatile (e.g., RAM, etc.) and/or non-volatile memory (e.g., ROM, flash memory, F-RAM, etc.).

Multi-functional circuitry 212 can be implemented as one or more chips and/or components (e.g., transmitter, receiver, transceiver, and/or other communication circuitry) that perform other functions such as local wireless communications, e.g., with sensor control device 102 under the appropriate protocol (e.g., Wi-Fi, Bluetooth, Bluetooth Low Energy, Near Field Communication (NFC), Radio Frequency Identification (RFID), proprietary protocols, and others) and determining the geographic position of reader device 120 (e.g., global positioning system (GPS) hardware). One or more other antennas 214 are associated with the functional circuitry 212 as needed to operate with the various protocols and circuits.

Power supply 216 can include one or more batteries, which can be rechargeable or single-use disposable batteries. Power management circuitry 218 can regulate battery charging and power supply monitoring, boost power, perform DC conversions, and the like.

Reader device 120 can also include or be integrated with a drug (e.g., insulin, etc.) delivery device such that they, e.g., share a common housing. Examples of such drug delivery devices can include medication pumps having a cannula that remains in the body to allow infusion over a multi-hour or multi-day period (e.g., wearable pumps for the delivery of basal and bolus insulin). Reader device 120, when combined with a medication pump, can include a reservoir to store the drug, a pump connectable to transfer tubing, and an infusion cannula. The pump can force the drug from the reservoir, through the tubing and into the diabetic's body by way of the cannula inserted therein. Other examples of drug delivery devices that can be included with (or integrated with) reader device 120 include portable injection devices that pierce the skin only for each delivery and are subsequently removed (e.g., insulin pens). A reader device 120, when combined with a portable injection device, can include an injection needle, a cartridge for carrying the drug, an interface for controlling the amount of drug to be delivered, and an actuator to cause injection to occur. The device can be used repeatedly until the drug is exhausted, at which point the combined device can be discarded, or the cartridge can be replaced with a new one, at which point the combined device can be reused repeatedly. The needle can be replaced after each injection.

The combined device can function as part of a closed-loop system (e.g., an artificial pancreas system requiring no user intervention to operate) or semi-closed loop system (e.g., an insulin loop system requiring seldom user intervention to operate, such as to confirm changes in dose). For example, the diabetic's analyte level can be monitored in a repeated automatic fashion by sensor control device 102, which can then communicate that monitored analyte level to reader device 120, and the appropriate drug dosage to control the diabetic's analyte level can be automatically determined and subsequently delivered to the diabetic's body. Software instructions for controlling the pump and the amount of insulin delivered can be stored in the memory of reader device 120 and executed by the reader device's processing circuitry. These instructions can also cause calculation of drug delivery amounts and durations (e.g., a bolus infusion and/or a basal infusion profile) based on the analyte level measurements obtained directly or indirectly from sensor control device 102. In some embodiments sensor control device 102 can determine the drug dosage and communicate that to reader device 120.

Example Embodiments of Sensor Control Devices

Figure 3:
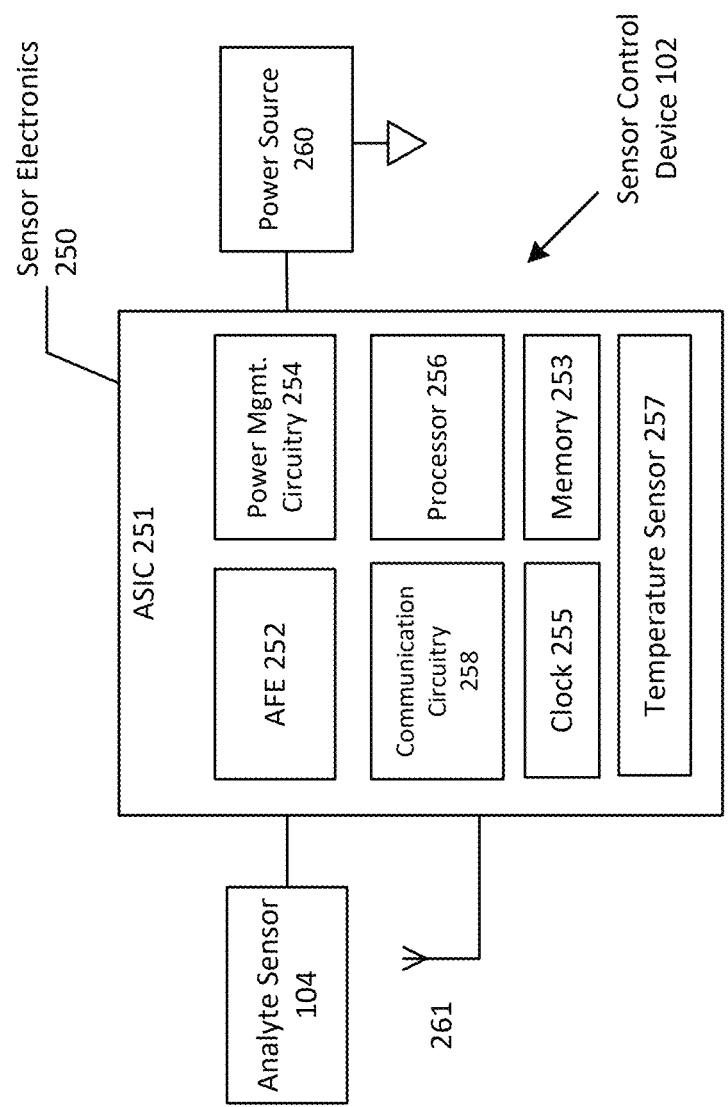
FIG. 3 is a block diagram of an example embodiment of a sensor control device.

FIG. 3 is a block diagram depicting an example embodiment of sensor control device 102 having analyte sensor 104 and sensor electronics 250 (including analyte monitoring circuitry) that can have the majority of the processing capability for rendering end-result data suitable for display to the user. In FIG. 3, a single semiconductor chip 251 is depicted that can be a custom application specific integrated circuit (ASIC). Shown within ASIC 251 are certain high-level functional units, including an analog front end (AFE) 252, power management (or control) circuitry 254, processor 256, and communication circuitry 258 (which can be implemented as a transmitter, receiver, transceiver, passive circuit, or otherwise according to the communication protocol). In this embodiment, both AFE 252 and processor 256 are used as analyte monitoring circuitry, but in other embodiments either circuit can perform the analyte monitoring function. Processor 256 can include one or more processors, microprocessors, controllers, and/or microcontrollers, each of which can be a discrete chip or distributed amongst (and a portion of) a number of different chips.

A memory 253 is also included within ASIC 251 and can be shared by the various functional units present within ASIC 251, or can be distributed amongst two or more of them. Memory 253 can also be a separate chip. Memory 253 is non-transitory and can be volatile and/or non-volatile memory. In this embodiment, ASIC 251 is coupled with power source 260, which can be a coin cell battery, or the like. AFE 252 interfaces with in vivo analyte sensor 104 and receives measurement data therefrom and outputs the data to processor 256 in digital form, which in turn can, in some embodiments, process in any of the manners described elsewhere herein. This data can then be provided to communication circuitry 258 for sending, by way of antenna 261, to reader device 120 (not shown), for example, where minimal further processing is needed by the resident software application to display the data. Antenna 261 can be configured according to the needs of the application and communication protocol. Antenna 261 can be, for example, a printed circuit board (PCB) trace antenna, a ceramic antenna, or a discrete metallic antenna. Antenna 261 can be configured as a monopole antenna, a dipole antenna, an F-type antenna, a loop antenna, and others.

Information may be communicated from sensor control device 102 to a second device (e.g., reader device 120) at the initiative of sensor control device 102 or reader device 120. For example, information can be communicated automatically and/or repeatedly (e.g., continuously) by sensor control device 102 when the analyte information is available, or according to a schedule (e.g., about every 1 minute, about every 5 minutes, about every 10 minutes, or the like), in which case the information can be stored or logged in a memory of sensor control device 102 for later communication. The information can be transmitted from sensor control device 102 in response to receipt of a request by the second device. This request can be an automated request, e.g., a request transmitted by the second device according to a schedule, or can be a request generated at the initiative of a user (e.g., an ad hoc or manual request). In some embodiments, a manual request for data is referred to as a "scan" of sensor control device 102 or an "on-demand" data transfer from device 102. In some embodiments, the second device can transmit a polling signal or data packet to sensor control device 102, and device 102 can treat each poll (or polls occurring at certain time intervals) as a request for data and, if data is available, then can transmit such data to the second device. In many embodiments, the communication between sensor control device 102 and the second device are secure (e.g., encrypted and/or between authenticated devices), but in some embodiments the data can be transmitted from sensor control device 102 in an unsecured manner, e.g., as a broadcast to all listening devices in range.

Different types and/or forms and/or amounts of information may be sent as part of each communication including, but not limited to, one or more of current sensor measurements (e.g., the most recently obtained analyte level information temporally corresponding to the time the reading is initiated), rate of change of the measured metric over a predetermined time period, rate of the rate of change of the metric (acceleration in the rate of change), or historical metric information corresponding to metric information obtained prior to a given reading and stored in a memory of sensor control device 102.

Some or all of real time, historical, rate of change, rate of rate of change (such as acceleration or deceleration) information may be sent to reader device 120 in a given communication or transmission. In certain embodiments, the type and/or form and/or amount of information sent to reader device 120 may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments reader device 120 can output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of sensor control device 102 (e.g., in the form of a graphical trace). Additionally, an on-skin or sensor temperature reading or measurement may be collected by an optional temperature sensor 257. Those readings or measurements can be communicated (either individually or as an aggregated measurement over time) from sensor control device 102 to another device (e.g., reader 120). The temperature reading or measurement, however, may be used in conjunction with a software routine executed by reader device 120 to correct or compensate the analyte measurement output to the user, instead of or in addition to actually displaying the temperature measurement to the user.

Embodiments of Systems, Devices and Methods for Sensor Fault Detection

Example Characterizations of a Sensor Fault in an Analyte Sensor

In vivo analyte sensors can be configured to sense one or more characteristics in a living body. One characteristic, for example, is an analyte level (e.g., a glucose level), which is a measure of the analyte concentration in a bodily fluid or gas. For electrochemical sensors, the presence of an analyte in a bodily fluid can cause the sensor to generate a response in the form of an electrical current (amperometric) or an electrical charge (coulometric). For other types of sensors, a response can be in a different form, such as a photonic intensity (e.g., optical light). The responsiveness of an analyte sensor can be adversely affected by various factors, including, but not limited to, vascular processes, biofouling, fibrous encapsulation, interference by neutrophils, or other immunological reactions at the site of the sensor insertion over time.

Figure 4:
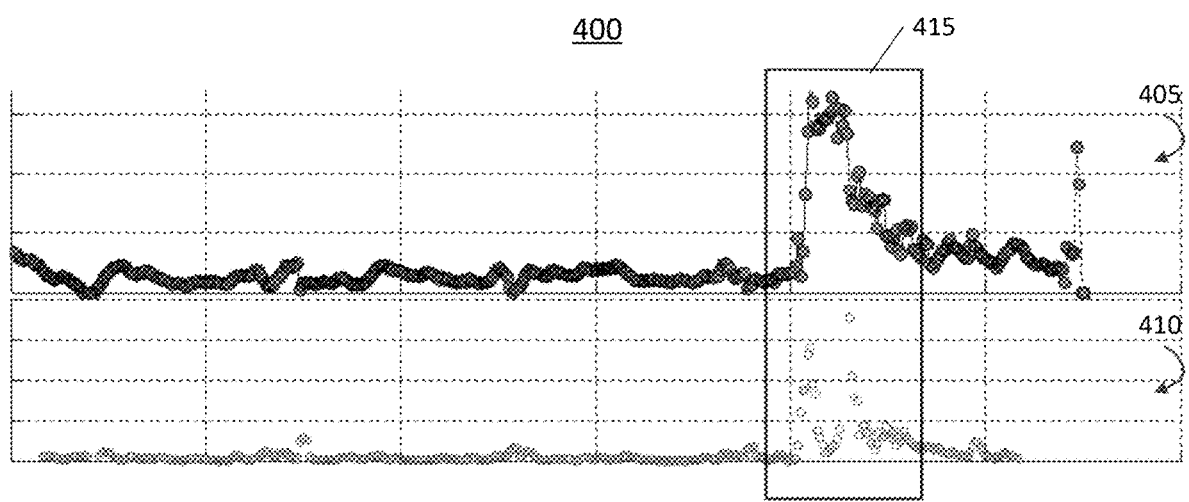
FIG. 4 is a graph depicting example analyte measurements over time.

Referring to FIG. 4, graph 400 depicts example analyte measurements from an in vivo analyte sensor over time. In particular, upper plot 405 shows analyte level readings over time, while lower plot 410 shows rates of change over the same time period. According to graph 400, black rectangle 415 indicates analyte measurements during a period of time in which a leak-associated sensor fault has occurred. As can be seen in FIG. 4, during the time period indicated by rectangle 415, both analyte level readings and rates of change are relatively high.

Example Embodiments Using Analyte Level Metrics and Thresholds for Sensor Fault Detection Example embodiments of methods for sensor fault detection based on analyte level metrics and thresholds will now be described. Before doing so, it will be understood by those of skill in the art that any one or more of the steps of the example methods described herein can be stored as software instructions in a non-transitory memory of a sensor control device, a reader device, a remote computer, or a trusted computer system, such as those described with respect to FIG. 1. The stored instructions, when executed, can cause the processing circuitry of the associated device or computing system to perform any one or more of the steps of the example methods described herein. It will also be understood by those of skill in the art that, in many of the embodiments, any one or more of the method steps described herein, including the calculation of analyte metrics and/or the determination of a sensor fault, can be performed using real-time sensor data, near real-time sensor data, or historical sensor data.

It will also be appreciated by those of skill in the art that the instructions can be stored in non-transitory memory on a single device (e.g., a sensor control device or a reader device) or, in the alternative, can be distributed across multiple discrete devices, which can be located in geographically dispersed locations (e.g., a cloud platform). Likewise, those of skill in the art will recognize that the representations of computing devices in the embodiments disclosed herein, such as those shown in FIG. 1, are intended to cover both physical devices and virtual devices (or "virtual machines").

Figure 5:
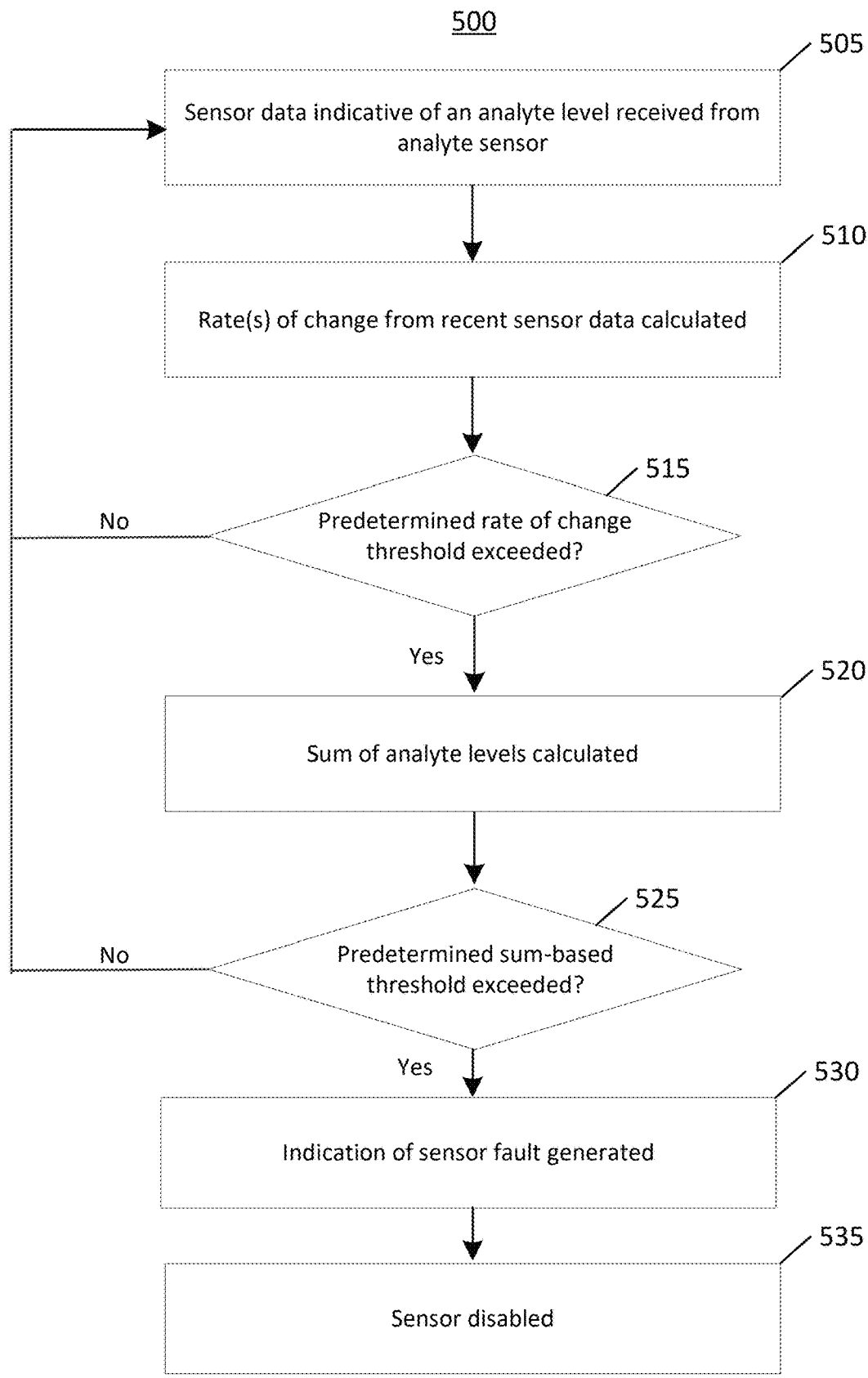
FIG. 5 is a flow diagram depicting an example embodiment of a method for fault detection in an analyte sensor.

FIG. 5 is a flow diagram depicting an example embodiment of a method 500 for sensor fault detection in an analyte sensor. At Step 510, sensor data indicative of an analyte level, such as a glucose level, is received from an analyte sensor. As described with respect to FIG. 1, the analyte sensor can include at least a portion that is inserted into a user's body. At Step 520, a rate of change from recent sensor data is calculated. In some embodiments, a first rate of change, V1, at a particular time, k, can be calculated according to the following equation: $V1(k)=[g(k)-g(k-T1)]/T1$, where g is the analyte level and T1 is a unit of time.

According to some embodiments, at Step 510, multiple rates of change can be calculated for sensor data received from the analyte sensor. As one example, if four rates of change are to be calculated at Step 510, then a second rate of change, V2, can be calculated according to the following equation: $V2(k)=[g(k)-g(k-T2)]/T2$. Similarly, rates of change for $V3(k)$ and $V4(k)$ can be calculated, respectively, using the equations $V3(k)=[g(k)-g(k-T3)]/T3$ and $V4(k)=[g(k)-g(k-T4)]/T4$. Those of skill in the art will recognize that other numbers of rates of change (e.g., 5, 6, 7, etc.) can be calculated and are fully within the scope of the present disclosure.

At Step 515 of FIG. 5, the calculated rate(s) of change from Step 510 are compared to a predetermined rate of change threshold. According to some embodiments, the predetermined rate of change threshold can be compared to an absolute value of the calculated rate(s) of change. If the predetermined rate of change threshold is not exceeded, then method 500 returns to Step 505.

Referring still to method 500 of FIG. 5, if any of the calculated rate(s) of change exceed the predetermined rate of change threshold, then at Step 520, a sum of the analyte level values S(k) within a predetermined time window is calculated according to the following equation: $S(k)=g(k)+g(k-T1)$, where g is the analyte level and T1 is a unit of time.

At Step 525 of FIG. 5, the calculated sum of the analyte level values is compared to a predetermined sum-based threshold. If the calculated sum of the analyte levels does not exceed the predetermined sum-based threshold, then method 500 returns to Step 505. If the calculated sum of the analyte levels exceeds the predetermined sum-based threshold, then at Step 530, an indication of a sensor fault is generated. According to some embodiments, if the indication of the sensor fault is generated, a notification can be outputted to the user. In some embodiments, for example, the notification can be a visual and/or auditory indication to the user that a sensor fault has been detected. In other embodiments, the notification can be a request displayed to the user via a graphical user interface, for example, to remove and/or replace the analyte sensor. In some embodiments, at Step 535, the sensor is disabled.

Those of skill in the art will also appreciate that, in some embodiments, method 500 can be implemented by first calculating the sum of analyte levels and comparing the calculated sum to a predetermined sum-based threshold (Steps 520, 525), and, thereafter calculating the rate(s) of change and comparing the rate(s) of change to a predetermined rate of change threshold (Steps 510, 515).

In other embodiments, the sum of analyte levels and rate(s) of change can be calculated and compared to their respective thresholds simultaneously, or in a near simultaneous fashion. It will be understood by those of skill in the art that if both thresholds are exceeded, then an indication of sensor fault is generated at Step 530.

According to another embodiment, the rate-based check at Step 515 can be performed at time, k1, while the sum-based check at Step 525 can be performed at time, k2. If the two conditions are met, then a time differential between k1 and k2 is calculated. If the calculated time differential is within a predetermined time differential threshold, then an indication of sensor fault is generated at Step 530.

According to another embodiment of method 500, the rate-based check at Step 515 can be assessed from any combination of all possible rates of change within a time window around the evaluation instance, k1. For example, given points k1, k1-T1, and k1-T3, the absolute rates of change can be calculated based on the pairs (k1, k1-T1), (k1-T1, k1-T2), (k1-T2, k1-T3). In some embodiments, the absolutes rates of change can also be calculated based on any non-adjacent combinations, e.g., (k1, k1-T2). Those of skill in the art will appreciate that rate(s) of change from other time instances can be utilized for comparison to the predetermined rate of change threshold, and are fully within the scope of the present disclosure.

Referring still to FIG. 5, according to another embodiment of method 500, at Step 515, instead of comparing the highest absolute rate of change to the predetermined rate of change threshold, a central tendency (e.g., mean, median, or mode) of the multiple rates of change can be compared to the predetermined rate of change threshold. In some embodiments, the central tendency value can be based on the absolute rates of change for the sensor data received from the analyte sensor.

For each and every embodiment of a method disclosed herein, systems and devices capable of performing each of those embodiments are covered within the scope of the present disclosure. For example, embodiments of sensor control devices are disclosed, and these devices can have one or more analyte sensors, analyte monitoring circuits (e.g., an analog circuit), memories (e.g., for storing instructions), power sources, communication circuits, transmitters, receivers, clocks, counters, times, temperature sensors, processors (e.g., for executing instructions) that can perform any and all method steps or facilitate the execution of any and all method steps. These sensor control device embodiments can be used and can be capable of use to implement those steps performed by a sensor control device from any and all of the methods described herein. Similarly, embodiments of reader devices are disclosed, and these devices can have one or more memories (e.g., for storing instructions), power sources, communication circuits, transmitters, receivers, clocks, counters, times, and processors (e.g., for executing instructions) that can perform any and all method steps or facilitate the execution of any and all method steps. These reader device embodiments can be used and can be capable of use to implement those steps performed by a reader device from any and all of the methods described herein. Embodiments of computer devices and servers are disclosed, and these devices can have one or more memories (e.g., for storing instructions), power sources, communication circuits, transmitters, receivers, clocks, counters, times, and processors (e.g., for executing instructions) that can perform any and all method steps or facilitate the execution of any and all method steps. These reader device embodiments can be used and can be capable of use to implement those steps performed by a reader device from any and all of the methods described herein.

Computer program instructions for carrying out operations in accordance with the described subject matter may be written in any combination of one or more programming languages, including an object oriented programming language such as Java, JavaScript, Smalltalk, C++, C #, Transact-SQL, XML, PHP or the like and conventional procedural programming languages, such as the "C" programming language or similar programming languages. The program instructions may execute entirely on the user's computing device, partly on the user's computing device, as a stand-alone software package, partly on the user's computing device and partly on a remote computing device or entirely on the remote computing device or server. In the latter scenario, the remote computing device may be connected to the user's computing device through any type of network, including a local area network (LAN) or a wide area network (WAN), or the connection may be made to an external computer (for example, through the Internet using an Internet Service Provider).

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the foregoing description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An analyte monitoring system, comprising:
  a sensor control device including an analyte sensor at least a portion of which is configured to be inserted into a user's body, first processing circuitry, and a first non-transitory memory, wherein the sensor control device is configured to collect sensor data indicative of an analyte level from the analyte sensor; and
  a reader device comprising a second processing circuitry and a second non-transitory memory,
  wherein at least one of the first or the second non-transitory memory includes instructions that, when executed, cause the at least one of the first or the second processing circuitry to:
    calculate a rate of change metric based on the collected sensor data, wherein the rate of change metric is calculated at a first time;
    calculate a sum of analyte levels metric based on the collected sensor data, wherein the sum of analyte levels metric is calculated at a second time;
    compare the rate of change metric with a first threshold and compare the sum of analyte levels metric with a second threshold; and
    in response to a determination that the rate of change metric exceeds the first threshold, that the sum of analyte levels metric exceeds the second threshold, and that a difference between the first time and the second time is less than a predetermined time threshold, generate an indication of a sensor fault.

2. The analyte monitoring system of claim 1, wherein the rate of change metric is a function of a plurality of rate of change values.

3. The analyte monitoring system of claim 2, wherein the rate of change metric is a central tendency of the plurality of rate of change values.

4. The analyte monitoring system of claim 1, wherein the rate of change metric is based on the collected sensor data within a predetermined time window.

5. The analyte monitoring system of claim 4, wherein the rate of change metric is based on two consecutive analyte data points of the collected sensor data within the predetermined time window.

6. The analyte monitoring system of claim 4, wherein the rate of change metric is based on two non-consecutive analyte data points of the collected sensor data within the predetermined time window.

7. The analyte monitoring system of claim 1, wherein the instructions to compare the rate of change metric to the first threshold comprises instructions to compare an absolute value of the rate of change metric to the first threshold.

8. The analyte monitoring system of claim 4, wherein the sum of analyte levels metric comprises a sum of analyte level measurements within a second predetermined time window.

9. The analyte monitoring system of claim 1, wherein the instructions, when executed, further cause the at least one of the first or the second processing circuitry to output a notification to a display of the reader device.

10. The analyte monitoring system of claim 9, wherein the notification comprises a visual or auditory indication that the sensor fault was detected.

11. The analyte monitoring system of claim 1, wherein the instructions, when executed, further cause the at least one of the first or the second processing circuitry to disable the analyte sensor.

12. A computer-implemented method for detecting a sensor fault, the method comprising:
  collecting, by a sensor control device comprising an analyte sensor at least a portion of which is inserted into a user's body, sensor data indicative of an analyte level;
  calculating a rate of change metric based on the collected sensor data, wherein the rate of change metric is calculated at a first time;
  calculating a sum of analyte levels metric based on the collected sensor data, wherein the sum of analyte levels metric is calculated at a second time;
  comparing the rate of change metric with a first threshold and comparing the sum of analyte levels metric with a second threshold; and
  in response to determining that the rate of change metric exceeds the first threshold, that the sum of analyte levels metric exceeds the second threshold, and that a difference between the first time and the second time is less than a predetermined time threshold, generating an indication of the sensor fault.

13. The method of claim 12, wherein the rate of change metric is based on the collected sensor data within a predetermined time window.

14. The method of claim 13, wherein the sum of analyte levels metric comprises a sum of analyte level measurements within a second predetermined time window.

15. The method of claim 12, wherein the rate of change metric is a central tendency of a plurality of rate of change values.

16. The method of claim 12, further comprising transmitting, by a wireless communication circuitry of the sensor control device, the collected sensor data to a reader device.

17. The method of claim 16, further comprising outputting a notification to a display of the reader device.

18. The method of claim 12, further comprising disabling the analyte sensor.

* * * * *